United States Patent
Jan

(10) Patent No.: US 10,429,671 B2
(45) Date of Patent: Oct. 1, 2019

(54) OPHTHALMIC LENS AND MANUFACTURING METHOD THEREOF

(71) Applicant: BenQ Materials Corporation, Taoyuan (TW)

(72) Inventor: Fan-Dan Jan, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 80 days.

(21) Appl. No.: 15/912,582

(22) Filed: Mar. 6, 2018

(65) Prior Publication Data

US 2019/0155054 A1    May 23, 2019

(30) Foreign Application Priority Data

Nov. 17, 2017   (TW) .............................. 106139853 A

(51) Int. Cl.
| | | |
|---|---|---|
| *G02C 7/04* | (2006.01) | |
| *A61L 27/34* | (2006.01) | |
| *A61L 27/54* | (2006.01) | |
| *G02B 1/14* | (2015.01) | |
| *G02B 1/04* | (2006.01) | |
| *G02C 7/02* | (2006.01) | |
| *G02B 1/18* | (2015.01) | |
| *A61F 2/16* | (2006.01) | |
| *B29D 11/00* | (2006.01) | |
| *G02B 1/12* | (2006.01) | |

(52) U.S. Cl.
CPC .............. *G02C 7/049* (2013.01); *A61L 27/34* (2013.01); *A61L 27/54* (2013.01); *G02B 1/043* (2013.01); *G02B 1/14* (2015.01); *G02C 7/028* (2013.01); *A61F 2/1613* (2013.01); *A61L 2300/216* (2013.01); *A61L 2430/16* (2013.01); *B29D 11/00038* (2013.01); *G02B 1/12* (2013.01); *G02B 1/18* (2015.01)

(58) Field of Classification Search
CPC ....................................................... G02B 1/043
See application file for complete search history.

(56) References Cited

U.S. PATENT DOCUMENTS

| | | | |
|---|---|---|---|
| 8,911,831 B2* | 12/2014 | Messersmith | A61L 27/34 210/702 |
| 2013/0118127 A1* | 5/2013 | Kolluru | B65B 5/04 53/431 |
| 2014/0336040 A1* | 11/2014 | Yan | C08G 73/0688 502/159 |
| 2017/0355799 A1* | 12/2017 | Veiseh | C08F 230/02 |

FOREIGN PATENT DOCUMENTS

| | | | |
|---|---|---|---|
| JP | P2013-514841 A | 5/2013 | |
| WO | WO2016187698 A1 | 1/2016 | |
| WO | WO-2016187698 A1 * | 12/2016 | .............. C08J 7/047 |

OTHER PUBLICATIONS

Ren, P.-F.; Yang, H.-C.; Liang, H.-Q.; Xu, X.-L.; Wan, L.-S.; Xu, Z.-K. Langmuir 2015, 31, 5851-5858. American Chemical Society.*

* cited by examiner

*Primary Examiner* — Michael F Pepitone

(57) ABSTRACT

The invention is to provide an ophthalmic lens and a manufacturing method thereof. The ophthalmic lens comprises a lens body and an antimicrobial hydrophilic layer thereon, wherein the antimicrobial hydrophilic layer comprises tannic acid and a zwittericionic polymer. The zwittericionic polymer can be selected from one of the group consisting of a phosphorylcholine polymer, a sulfobetaine polymer, a carboxybetaine polymer and a mixed-charge polymer or combinations thereof.

14 Claims, No Drawings

OPHTHALMIC LENS AND MANUFACTURING METHOD THEREOF

CROSS-REFERENCE TO RELATED APPLICATION

This application claims the priority benefit of Taiwanese application serial No. 106139853, filed on, Nov. 17, 2017, which is incorporated herein by reference.

BACKGROUND OF THE INVENTION

Field of the Invention

The present invention relates to an ophthalmic lens and the method for manufacturing the same and particularly, relates to an ophthalmic lens having excellent deposit resistance and high hydrophilicity and a method for manufacturing the same.

Description of Related Art

In the early years, hard contact lens was mainly made of glass. The soft contact lens was therefore developed to improve the wearing discomfort of the hard contact lens. The soft contact lens can be classified into two categories, hydrogel contact lens and silicone hydrogel contact lens.

The increasing surface hydrophilicity of contact lens will increase the wearing comfort of contact lens. However, the increasing surface hydrophilicity of the contact lens will also increase the deposition of the protein and lipid in the tears onto the surface of the contact lens, thus results in reduction of the clarity of lens and the wearing comfort and even the occurrence of ocular allergy. Moreover, the bacteria on users' fingers are usually transferred to the soft contact lens and adhering thereon during wearing the contact lens, which will result in ocular infection thereafter. Therefore, there is a need for an ophthalmic lens with high hydrophilicity, deposit resistance and antimicrobial properties.

Several methods have been proposed in the state of the art to solve the problem of protein and/or lipid deposition, such as adding fluoro-containing monomers or zwitterionic materials into the composition for manufacturing the ophthalmic lens; treating the surface of the contact lens by plasma treatment; or modifying the surface of the contact lens by, for example, covalently bonding zwitterionic materials to the surface of the contact lens. The approaches mentioned above have various disadvantages. For example, it is known that the addition of fluoro-containing monomers to the composition for manufacturing the ophthalmic lens will lower the surface hydrophilicity of the formed lens; the addition of zwitterionic materials into the composition for manufacturing the ophthalmic lens will adversely affect the physical properties of ophthalmic lens and decrease the production yield; plasma treatment is conducted by high-cost equipment; the modification of lens surface will cause lens deformation and/or decrease the production yield and needs further cleaning step so that the manufacturing process thereof is complicated.

Recently, bio-compatible materials are widely used in medical devices, especially the bio-polymer materials. It proposes the use of polydopamine to modify the surface of the contact lens. However, because the color of the polydopamine is dark-blue, thus a brown hydrophilic layer will be formed on the polydopamine-modified surface of the contact lens. Therefore it suggests to control the concentration of the polydopamine for modifying the surface of contact lens in order to reduce the impact the optical properties of the contact lens.

Therefore, the present invention is to provide an ophthalmic lens having a novel antimicrobial hydrophilic layer which provides excellent deposit resistance, high hydrophilicity and desirable optical property, and a simple and high effective method for manufacturing the ophthalmic lens.

SUMMARY OF THE INVENTION

The present invention is to provide an ophthalmic lens having a novel antimicrobial hydrophilic layer which provides excellent deposit resistance, high hydrophilicity and desirable optical property, and a simple and high effective method for manufacturing the ophthalmic lens. The present ophthalmic lens comprises an antimicrobial hydrophilic layer comprising tannic acid and a zwitterionic polymer formed on the surface of the lens. The zwitterionic polymer in the antimicrobial hydrophilic layer can prevent proteins, lipids and bacteria from depositing and/or adhering onto the ophthalmic lens to achieve an excellent deposit resistance and high antimicrobial properties. Moreover, the tannic acid in the antimicrobial hydrophilic layer can enhance the biocompatibility and hydrophility, thus the wearing comfortability of the present ophthalmic lens can be enhanced.

According to an aspect of the present invention, an ophthalmic lens comprising a lens body and a novel antimicrobial hydrophilic layer formed on the surface of the lens body is provided. The antimicrobial hydrophilic layer comprises tannic acid and a zwitterionic polymer, wherein the zwitterionic polymer is selected from one of the group consisting of a phosphorylcholine polymer, a sulfobetaine polymer, a carboxybetaine polymer and a mixed-charge polymer, or combinations thereof.

In a preferred embodiment of the present invention, the zwitterionic polymer can be selected from one of the group consisting of poly(2-methacryloyloxyethyl phosphorylcholine) (PMPC), poly(sulfobetaine methacrylate) (PSBMA) and poly(carboxybetaine methacrylate) (PCBMA), or combinations thereof.

In a preferred embodiment of the present invention, the weight average molecular weight of the zwitterionic polymer is in the range of 10,000 to 300,000, and preferably in the range of 20,000 to 250,000.

In a preferred embodiment of the present invention, the lens body is made of a hydrogel or a silicon hydrogel.

According to another aspect of the present invention, a simple and high effective method for manufacturing an ophthalmic lens is provided. The ophthalmic lens manufactured by the method has excellent deposit resistance and high hydrophilicity.

The method for manufacturing the ophthalmic lens comprises steps of: (a) providing a lens body; (b) immersing the lens body in a tannic acid solution, wherein the tannic acid solution comprises polydopamine; and (c) immersing the tannic acid treated lens body in a zwitterionic polymer solution, the zwitterionic polymer can be selected from one of the group consisting of a phosphorylcholine polymer, a sulfobetaine polymer, a carboxybetaine polymer and a mixed-charge polymer, or combinations thereof.

In a preferred embodiment of the method of the present invention, the zwitterionic polymer can be selected from one of the group consisting of poly(2-methacryloyloxyethyl phosphorylcholine) (PMPC), poly(sulfobetaine methacrylate) (PSBMA) and poly(carboxybetaine methacrylate) (PCBMA), or combinations thereof.

In a preferred embodiment of the method of the present invention, in the step of (b), the concentration of the tannic acid solution is between 250 ppm to 2500 ppm and is preferably between 300 ppm to 2000 ppm. The concentration of the polydopamine in the tannic acid solution can be between 1 ppm to 20 ppm and is preferably between 2 ppm to 12 ppm.

In a preferred embodiment of the method of the present invention, in the step of (b), the tannic acid solution comprising the lens body can be heated to a temperature of 30° C. to 80° C., and preferably heated to a temperature of 40° C. to 65° C. for a time in the range of 5 minutes to 60 minutes and preferably in the range of 10 minutes to 30 minutes.

In a preferred embodiment of the method of the present invention, in the step of (c), the concentration of the zwitterionic polymersolution is between 500 ppm to 3000 ppm and is preferably between 750 ppm to 2500 ppm. When the lens body is immersed in the zwitterionic polymer solution, the zwitterionic polymer solution can be heated to a temperature of 40° C. to 120° C. and preferably to a temperature of 60° C. to 85° C. The lens body can be immersed in the zwitterionic polymer solution for a time in the range of 30 minutes to 120 minutes, and preferably in the range of 50 minutes to 90 minutes.

In a preferred embodiment of the method of the present invention, the weight average molecular weight of the zwitterionic polymer is in the range of 10,000 to 300,000, and preferably in the range of 20,000 to 250,000.

The method for manufacturing the ophthalmic lens of the present invention can further comprises a step of conducting a sterilization treatment and packaging process for the ophthalmic lens. After the lens body is treated by tannic acid and zwitterionic polymer solutions, the treated lens body can be immersed in a phosphate buffer solution to conduct a sterilization treatment and packing process.

In another preferred embodiment of the method of the present invention, the tannic acid solution of step (b) can be mixed with the zwitterionic polymer solution of step (c). The concentration of the tannic acid in the mixed solution can be between 150 ppm and 1200 ppm and preferably between 200 ppm and 1000 ppm, and the concentration of the zwitterionic polymer can be between 150 ppm and 1200 ppm and preferably between 200 ppm and 1000 ppm. Polydopamine can be added into the mixed solution of tannic acid and zwitterionic polymer, the concentration of the polydopamine can be in the range of 0.5 ppm to 20 ppm and preferably in the range of 1 ppm to 15 ppm.

In another preferred embodiment of the method of the present invention, when the lens body is immersed in the mixed solution of tannic acid and zwitterionic polymer, the mixed solution can be heated to a temperature of 30° C. to 80° C. and preferably between 40° C. and 65° C. for 5 minutes to 60 minutes and preferably for 10 minutes to 30 minutes.

The above and other aspects of the invention will become better understood with regard to the following detailed description of the preferred but non-limiting embodiment(s). These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be affected without departing from the spirit and scope of the novel concepts of the disclosure.

DETAILED DESCRIPTION OF THE INVENTION

In the following detailed description, for purposes of explanation, numerous specific details are set forth in order to provide a thorough understanding of the disclosed embodiments. It will be apparent, however, that one or more embodiments may be practiced without these specific details.

It is apparent that departures from specific designs and methods described and shown will suggest themselves to those skilled in the art and may be used without departing from the spirit and scope of the invention. The present invention is not restricted to the particular constructions described and illustrated, but should be construed to cohere with all modifications that may fall within the scope of the appended claims.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

The present invention is to provide an ophthalmic lens comprising a lens body and a novel antimicrobial hydrophilic layer on the surface of the lens body.

In an embodiment of the present invention, the lens body is made of a hydrogel material. The hydrogel material comprises but not limited to at least one hydrophilic monomer, a cross-linking agent and an initiator.

Suitable hydrophilic monomers can be, such as N-vinylpyrrolidone (NVP), 2-hydroxyethyl methacrylate (HEMA), N,N'-dimethylacrylamide (DMA), methyl acrylic acid (MAA), N,N'-diethylacrylamide, N-isopropylamide, 2-Hydroxypropyl acrylate, vinyl acetate, N-acrylolmorpholine, 2-dimethylaminoethyl acrylate or combinations thereof, but not limited thereto.

Suitable initiators can be the initiator suitably used in conventional ophthalmic lens materials, for example, thermal initiator or photo initiator. Suitable thermal initiator can be but not limited to, for example, 2,2'-azobis(2,4-dimethylvaleronitrile) (ADVN), 2,2'-azobis(isobutyronitrile) (AIBN), 2,2'-azobis(2,4-dimethylvaleronitrile), 2,2'-azobis(2-methyl-propanenitrile), 2,2'-azobis(2-methyl-butanenitrile) or benzoyl peroxide. Suitable photo initiator can be but not limited to, for example, 2,4,6-trimethylbenzoyl diphenyl oxide, 2-hydroxy-2-methylpropiophenone, ethyl(2,4,6-trimethylbenzoly)phenylphosphinate or 2,2-diethoxyacetophenone.

Suitable cross-linking agents can be, for example, ethylene glycol dimethacrylate (EGDMA), trimethylolpropane trimethacrylate (TMPTA), triethylene ethylene glycol dimethacrylate (TEGDMA), tetraethylene ethylene glycol dimethacrylate (TrEGDMA), Poly(ethylene glycol) dimethacrylate, trimethylpropane trimethacrylate, vinyl methacrylate, ethylenediamine dimethyl acrylamide, glyceryl methacrylate, triallyisocyanurate, triallyl cyanurate or combinations thereof.

In another embodiment of the present invention, the lens body is made of a silicone hydrogel. The silicone hydrogel comprises but not limited to at least one siloxane macromer, at least one hydrophilic monomer and an initiator. Suitable siloxane macromers can be the siloxane macromes suitably used in conventional ophthalmic lens materials, particularly the siloxane macromers suitably used in conventional contact lens materials. The silicone hydrogel can further include but not limited to a cross-linking agent, a dye, a UV-blocking agent, a solvent or combinations thereof as needed.

In a preferred embodiment of the present invention, the antimicrobial hydrophilic layer comprises tannic acid and a zwitterionic polymer.

It is well known that tannic acid, one of plant polyphenols, is biocompatible and degradable. Tannic acid can be used as an antioxidant, a free radical scavenger, an antimicrobial agent or a deodorant due to the bio-properties given by its polyphenol structure. Recently, several studies have shown that tannic acid can form a thin film on a variety of materials to enhance the hydrophilicity and chemical properties of the surface thereof due to a large number of hydroxyl groups and phenolic groups of tannic acid. In addition, due to a large number of hydroxyl groups, tannic acid can graft to, copolymerize with or blending with other polymer materials via hydrogen bonds or covalent bonds. Therefore, the tannic acid provides a large number of hydroxyl groups and phenolic groups on the surface of the lens body so as to enhance the hydrophilicity and chemical versatility thereof.

In one embodiment of the present invention, polydopamine can be added into the tannic acid solution to enhance the adhesion between tannic acid and the surface of the lens body.

The zwitterionic polymer in the antimicrobial hydrophilic layer of the ophthalmic lens of the present invention is non-covalently bonded to the tannic acid, wherein the non-covalent bond can be, such as hydrogen bond, van der Waals' force, stacking force or combinations thereof.

The zwitterionic polymer is a polymer having both positively charged groups and negatively charged groups. The zwitterionic polymer has the properties of, such as, high hydrophilicity, good thermo- and chemical-stability, excellent biocompatibility and protein adhesion resistance. Therefore, deposit resistance and antimicrobial properties of the ophthalmic lens can be improved by modifying the surface of the ophthalmic lens with a zwitterionic polymer.

Suitable zwitterionic polymers can be but not limited to a phosphorylcholine polymer, a sulfobetaine polymer, a carboxybetaine polymer, a mixed-charge polymer or combinations thereof. In an embodiment of the present invention, the zwitterionic polymer can be poly(2-methacryloyloxyethyl phosphorylcholine) (PMPC), poly(sulfobetaine methacrylate) (PSBMA), poly(carboxybetaine methacrylate) (PCBMA) or combinations thereof.

In an embodiment of the present invention, a weight average molecular weight of the zwitterionic polymer is in the range of 10,000 to 300,000, and preferably in the range of 20,000 to 250,000.

The present ophthalmic lens comprises an antimicrobial hydrophilic layer comprising tannic acid and a zwitterionic polymer formed on the surface of the lens, wherein the tannic acid possesses highly hydrophilic and can be covalently bonded to the zwitterionic polymer. Because of the positive and the negative charge, zwitterions can prevent proteins, lipids, microorganisms from depositing on the surface of the ophthalmic lens. Moreover, the wearing comfortability of the present ophthalmic lens can be enhanced because the tannic acid in the antimicrobial hydrophilic layer enhances the biocompatibility and hydrophilicity.

Another aspect of the present invention is to provide a method for manufacturing an ophthalmic lens with excellent deposit resistance and high hydrophilicity. The method of the present invention is a simple and high effective method comprising the following steps but not limited thereto.

In an embodiment of the manufacture method of the present invention, a lens body of hydrogel or silicone hydrogel is provided. The lens body is immersed in a tannic acid solution which is added with polydopamine. The tannic acid treated lens body is taken out and immersed into a zwitterionic polymer solution in order to form an antimicrobial hydrophilic layer thereon.

In an embodiment of the manufacture method of the present invention, the concentration of the tannic acid solution is between 250 ppm to 2500 ppm and preferably between 300 ppm to 2000 ppm. The concentration of the polydopamine added into the tannic acid solution can be between 1 ppm to 20 ppm and is preferably between 2 ppm to 12 ppm.

In an embodiment of the manufacture method of the present invention, when the lens body is immersed in the tannic acid solution, the tannic acid solution can be heated to a temperature of 30° C. to 80° C. and preferably to a temperature of 40° C. to 65° C. for a time in the range of 5 minutes to 60 minutes and preferably in the range of 10 minutes to 30 minutes.

In an embodiment of the manufacture method of the present invention, the concentration of the zwitterionic polymer solution can be in the range of 500 ppm to 3000 ppm and preferably in the range of 750 ppm to 2500 ppm. When the lens body is immersed in the zwitterionic polymer solution, the zwitterionic polymer solution can be heated at the temperature in the range of 40° C. to 120° C., and preferably in the range of 60° C. to 85° C. The time for immersing the lens body in the zwitterionic polymer solution is in the range of 30 minutes to 120 minutes, and preferably in the range of 50 minutes to 90 minutes.

After the antimicrobial hydrophilic layer formed on the lens body through the above procedures, the lens body is washed by pure water to remove the tannic acid, polydopamine and zwitterionic polymer residues for about 5 minutes. The wash time can be varied in dependent to the practical conditions. After washing the lens body, a sterilization treatment and packing process can be conducted. The sterilization treatment suitably used in conventional method for manufacturing contact lens can be used in the method of the present invention, i.e. the treated lens with the antimicrobial hydrophilic layer is then immersed in a phosphate buffer solution to conduct a sterilization treatment and packing process.

According to one embodiment of the manufacture method of the present invention, the tannic acid solution can be mixed with the zwitterionic polymer solution. Polydopamine is added into the mixed solution of the tannic acid and the zwitterionic polymer.

According to another embodiment of the manufacture method of the present invention, the concentration of the tannic acid in the mixed solution of tannic acid and zwitterionic polymer can be from 150 ppm to 1200 ppm and preferably from 200 ppm to 1000 ppm. The concentration of the zwitterionic polymer in the mixed solution of tannic acid and zwitterionic polymer can be from 150 ppm to 1200 ppm and preferably from 200 ppm to 1000 ppm. The additive amount of the polydopamine in the mixed solution of tannic acid and zwitterionic polymer can be from 0.5 ppm to 20 ppm and preferably from 1 ppm to 15 ppm.

According to another embodiment of the manufacture method of the present invention, when the lens body is immersed in the mixed solution of tannic acid and zwitterionic polymer, the solution can be heated to a temperature of 30° C. to 80° C. and preferably to a temperature of 40° C. to 65° C. for 5 minutes to 60 minutes and preferably for 10 minutes to 30 minutes.

After an antimicrobial hydrophilic layer is formed on the lens body, the resulting lens body is washed as described above and then conducted a sterilization treatment and packaging process. The sterilization treatment suitably used in conventional method for manufacturing contact lens can be used in the method of the present invention, i.e., after the lens body is taken out from the immersing solution and is washed, the lens body is then immersed into a phosphate buffer solution to conduct a sterilization treatment and packing process.

The present invention will be explained in further detail with reference to the examples. However, the present invention is not limited to these examples.

PREPARATION EXAMPLE 1

Preparation of Polydopamine Solution 1 g of dopamine was dissolved in 1000 ml of aqueous sodium bicarbonate solution (pH is 8.5) and stirred for 24 hours. The resulting polydopamine solution with a concentration of 1000 ppm was obtained.

PREPARATION EXAMPLE 2

Preparation of Tannic Acid Solution 2 g of tannic acid (CAS No.:1401-55-4,obtained from ACROS Organics BVBA, Belgium) was dissolved in 1000 ml of deionized water and stirred for 30 minutes to obtain a tannic acid solution with a concentration of 2000 ppm.

PREPARATION EXAMPLE 3

Preparation of Poly(Sulfobetaine Methacrylate) Solution 5 g of sulfobetaine methacrylate (SBMA), 0.4 g of potassium persulfate and 100 g of deionized water were mixed in a flask to react at 70° C. for 24 hours. The resulting poly(sulfobetaine methacrylate) solution with a concentration of 5% was obtained. The weight average molecular weight of the poly(sulfobetaine methacrylate) is about 26,707.

PREPARATION EXAMPLE 4

Preparation of Silicon Hydrogel Lens Body 4.44 g of isophorone diisocyanate, 0.0025 g of dibutyltin dilaurate as the catalysts, and 40 mL of methylene chloride were added into a flask to form a solution, and the solution was stirred under a stream of nitrogen. Then, 20 g of α-butyl-ω-[3-(2,2-(hydroxymethyl)butoxy) propyl] polydimethylsiloxane was accurately weighed and added dropwise to the solution over about 1 hour. After the solution reacting at room temperature for 12 hours, the resulting reaction product was washed with a large amount of water, and then dehydrated and filtered to obtain a raw product. Then, the methylene chloride was evaporated to obtain a first siloxane macromer.

8.88 g of isophorone diisocyanate, 0.0025 g of dibutyltin dilaurate as the catalysts and 40 mL of methylene chloride were added into a flask to form a solution, and the solution was stirred under a stream of nitrogen. Then, 20 g of polydimethylsiloxane was accurately weighed and added dropwise to the solution over about 1 hour. After the solution reacting at room temperature for 12 hours, another 0.0025 g of dibutyltin dilaurate and 14.4 g of polyethylene glycol monomethacrylate were accurately weighed and added dropwisely to the solution over about 1 hour. After the solution reacting at room temperature for another 12 hours, the resulting reaction product was washed with a large amount of water, and then dehydrated and filtered to obtain a raw product. Then, the methylene chloride was evaporated to obtain a second siloxane macromer.

41.8 g of the first siloxane macromer, 6.3 g of the second siloxane macromer, 0.7 g of azobisisoheptonitrile (ADVN), 46.96 g of N-vinylpyrrodine (NVP), 6.3 g of 2-hydroxyethyl methacrylate (HEMA), 1 g of ethylene glycol dimethylacrylate (EGDMA) and 25.1 g of hexanol were mixed and stirred about 1 hour to form a mixture. Then, the mixture was injected into a mold of contact lens made of polypropylene (PP) and heated to initiate the radical polymerization thereof at 60° C. for 1 hour, 80° C. for 2 hours and 135° C. for 2 hours. After the polymerization was completed, the mold was immersed in 80% alcohol solution for 1 hour and the resulting molded lens was taken out of the mold to obtain a silicon hydrogel lens body.

EXAMPLE 1

First, the concentration of the polydopamine solution of Preparation Example 1 was diluted with aqueous sodium bicarbonate solution (pH=8.5) to 20 ppm. The tannic acid solution of Preparation Example 2 was diluted by deionized water to 1000 ppm. The poly(sulfobetaine methacrylate) solution of Preparation Example 3 was diluted by deionized water to 1000 ppm. Then, 2 ml of 20 ppm polydopamine solution, 2 ml of 1000 ppm tannic acid and 2 ml of 1000 ppm poly(sulfobetaine methacrylate) solution were mixed. The silicon hydrogel lens body of Preparation Example 4 was immersed in the mixed solution, and the mixed solution containing the lens was heated to 50° C. After 15 minutes, the lens body was taken out and washed by pure water to obtain the resulting lens. The resulting lens is determined the lens properties and antimicrobial properties. The test results are listed in Table 1.

EXAMPLE 2

First, the concentration of the polydopamine solution of Preparation Example 1 was diluted with aqueous sodium bicarbonate solution (pH=8.5) to 20 ppm. The poly(sulfobetaine methacrylate) solution of Preparation Example 3 was diluted by deionized water to 2000 ppm. 2 ml of 20 ppm polydopamine solution, 2 ml of 2000 ppm tannic acid of Preparation Example 2 and 2 ml of 2000 ppm poly(sulfobetaine methacrylate) solution were mixed. The silicon hydrogel lens body of Preparation Example 4 was immersed in the mixed solution, and the mixed solution containing the lens was heated to 50° C. After 15 minutes, the lens body was taken out and washed by pure water to obtain the resulting lens. The resulting lens is determined the lens properties and antimicrobial properties. The test results are listed in Table 1.

EXAMPLE 3

First, the concentration of the polydopamine solution of Preparation Example 1 was diluted with aqueous sodium bicarbonate solution (pH=8.5) to 5 ppm. The tannic acid solution of Preparation Example 2 was diluted by deionized water to 1000 ppm. The poly(sulfobetaine methacrylate)

solution of Preparation Example 3 was diluted by deionized water to 2000 ppm. 2 ml of 5 ppm polydopamine solution, 2 ml of 1000 ppm tannic acid and 2 ml of 2000 ppm poly(sulfobetaine methacrylate) solution were mixed. The silicon hydrogel lens body of Preparation Example 4 was immersed in the mixed solution, and the mixed solution containing the lens was heated to 50° C. After 15 minutes, the lens body was taken out and washed by pure water to obtain the resulting lens. The resulting lens is determined the lens properties and antimicrobial properties. The test results are listed in Table 1.

EXAMPLE 4

First, the concentration of the polydopamine solution of Preparation Example 1 was diluted with aqueous sodium bicarbonate solution (pH=8.5) to 5 ppm. The poly(sulfobetaine methacrylate) solution of Preparation Example 3 was diluted by deionized water to 1000 ppm. 2 ml of 5 ppm polydopamine solution, 2 ml of 2000 ppm tannic acid and 2 ml of 1000 ppm poly(sulfobetaine methacrylate) were mixed. The silicon hydrogel lens body of Preparation Example 4 was immersed in the mixed solution, and the mixed solution containing the lens was heated to 50° C. After 15 minutes, the lens body was taken out and washed by pure water. The resulting lens is determined the lens properties and antimicrobial properties. The test results are listed in Table 1.

EXAMPLE 5

First, the concentration of the polydopamine solution of Preparation Example 1 was diluted with aqueous sodium bicarbonate solution (pH=8.5) to 20 ppm. The tannic acid solution of Preparation Example 2 was diluted by deionized water to 1000 ppm. 2 ml of 20 ppm polydopamine solution and 2 ml of 1000 ppm tannic acid solution were mixed. The silicon hydrogel lens body of Preparation Example 4 was immersed in the mixed solution, and the mixed solution containing the lens was heated to 50° C. After 15 minutes, the lens body was taken out and washed by pure water.

Then, the poly(sulfobetaine methacrylate) solution of Preparation Example 3 was diluted by deionized water to 1000 ppm. The above-obtained lens was immersed in 4 ml of 1000 ppm poly(sulfobetaine methacrylate) solution. The poly(sulfobetaine methacrylate) solution containing the lens was heated to 80° C. for 60 minutes and then the lens was taken out, washed with pure water. The resulting lens is determined the lens properties and antimicrobial properties. The test results are listed in Table 1.

EXAMPLE 6

First, the concentration of the polydopamine solution of Preparation Example 1 was diluted with aqueous sodium bicarbonate solution (pH=8.5) to 20 ppm. 2 ml of 20 ppm polydopamine solution and 2 ml of 2000 ppm tannic acid solution were mixed. The silicon hydrogel lens body of Preparation Example 4 was immersed in the mixed solution, and the mixed solution containing the lens was heated to 50° C. After 15 minutes, the lens body was taken out and washed by pure water.

Then, the poly(sulfobetaine methacrylate) solution of Preparation Example 3 was diluted by deionized water to 2000 ppm. The above-obtained lens was immersed in 4 ml of 1000 ppm poly(sulfobetaine methacrylate) solution. The poly(sulfobetaine methacrylate) solution containing the lens was heated to 80° C. for 60 minutes and then the lens was taken out, washed with pure water. The resulting lens is determined the lens properties and antimicrobial properties. The test results are listed in Table 1.

EXAMPLE 7

First, the concentration of the polydopamine solution of Preparation Example 1 was diluted with aqueous sodium bicarbonate solution (pH=8.5) to 5 ppm. The tannic acid solution of Preparation Example 2 was diluted by deionized water to 1000 ppm. 2 ml of 5 ppm polydopamine solution and 2 ml of 1000 ppm tannic acid solution were mixed. The silicon hydrogel lens body of Preparation Example 4 was immersed in the mixed solution, and the mixed solution containing the lens was heated to 50° C. After 15 minutes, the lens body was taken out and washed by pure water.

Then, the poly(sulfobetaine methacrylate) solution of Preparation Example 3 was diluted by deionized water to 2000 ppm. The above-obtained lens was immersed in 4 ml of 2000 ppm poly(sulfobetaine methacrylate) solution. The poly(sulfobetaine methacrylate) solution containing the lens was heated to 80° C. for 60 minutes and then the lens was taken out, washed with pure water. The resulting lens is determined the lens properties and antimicrobial properties. The test results are listed in Table 1.

EXAMPLE 8

First, the concentration of the polydopamine solution of Preparation Example 1 was diluted with aqueous sodium bicarbonate solution (pH=8.5) to 5 ppm. 2 ml of 5 ppm polydopamine solution and 2 ml of 2000 ppm tannic acid solution were mixed. The silicon hydrogel lens body of Preparation Example 4 was immersed in the mixed solution, and the mixed solution containing the lens was heated to 50° C. After 15 minutes, the lens body was taken out and washed by pure water.

Then, the poly(sulfobetaine methacrylate) solution of Preparation Example 3 was diluted by deionized water to 1000 ppm. The above-obtained lens was immersed in 4 ml of 1000 ppm poly(sulfobetaine methacrylate) solution. The poly(sulfobetaine methacrylate) solution containing the lens was heated to 80° C. for 60 minutes and then the lens was taken out, washed with pure water. The resulting lens is determined the lens properties and antimicrobial properties. The test results are listed in Table 1.

COMPARATIVE EXAMPLE 1

The Comparative Example 1 was the silicone hydrogel lens body of Preparation Example 4, the surface of the lens body did not comprise an antimicrobial hydrophilic layer. The results of optical property, physical property, and antimicrobial tests of the ophthalmic lens were shown as the following Table 1.

The physical properties of the ophthalmic lens prepared from Example 1 to Example 8 and Comparative Example 1 were measured according to the following measuring method and the test results were shown in Table 1.

Measurement of the Contact Angle of the Ophthalmic Lens

The ophthalmic lens was immersed in water for 1 hour. Then, the ophthalmic lens was removed therefrom and taken to remove all surface water by wet wipe. After that, the contact angle of ophthalmic lens was measured by Contact Angle Wafer Surface Analysis Inspection Goniometer (VCA2500XE, commercially available from AST Products, USA).

Determination of Protein Adhesion

The ophthalmic lens was immersed in water for 1 hour. Then, the ophthalmic lens was removed therefrom and taken to remove all surface water by wet wipe. After that, the ophthalmic lens was immersed in a PP sample tube containing 3 ml of lysozyme solution and the PP sample tube was sealed by a PP protective cap and incubated at 37° C. for 48 hours. Next, the ophthalmic lens was removed therefrom and taken to remove all surface lysozyme solution by wet wipe. Then, the ophthalmic lens was immersed in a PP sample tube containing 2 ml lens extraction solution (the volume ratio of trifluoroacetic acid/acetonitrile/water was 1/500/500), and the sample tube was rotated by a rotary oscillator at 37° C. for 12 hours. Finally, the ophthalmic lens was removed therefrom and the protein adhesion was determined by measuring the weight of protein in the extraction solution.

Determination of Lipid Adhesion

The ophthalmic lens was immersed in water for 1 hour. Then, the ophthalmic lens was removed therefrom and taken to remove all surface water by wet wipe. After that, the ophthalmic lens was immersed in a PP sample tube containing 3 ml of cholesterol solution and the PP sample tube was sealed by a PP protective cap and incubated at 37° C. for 48 hours. Next, the ophthalmic lens was removed therefrom and taken to remove all surface cholesterol solution by wet wipe. Then, the ophthalmic lens was immersed in a PP sample tube containing 2 ml lens extraction solution (the volume ratio of trichloromethane/methanol was 2/1), and the sample tube was rotated by a rotary oscillator at 37° C. for 12 hours. Finally, the ophthalmic lens was removed therefrom and absorbance value was measured. The lipid adhesion of each lens was determined according to the lipid standard curve made from standard lipid concentration and absorbance value.

TABLE 1

The measurement results of Examples 1 to 8 and Comparative Example 1

| | Contact angle (°) | Protein Adhesion (µg) | Lipid Adhesion (µg) |
| --- | --- | --- | --- |
| Example1 | 19.1 | 23.22 | 0.65 |
| Example2 | 14.6 | 11.40 | 0.43 |
| Example3 | 17.9 | 12.24 | 0.58 |
| Example4 | 12.3 | 20.68 | 0.62 |
| Example5 | 31.4 | 25.74 | 1.12 |
| Example6 | 32.9 | 13.67 | 0.78 |
| Example 7 | 38.4 | 29.23 | 0.83 |
| Example 8 | 33.6 | 28.76 | 1.07 |
| Comparative Example1 | 121.5 | 28.71 | 1.32 |

From the test results shown in Table 1, either the protein adhesion, the lipid adhesion or both obtained in Examples 1 to 8 were lower than those obtained in Comparative Example 1. The ophthalmic lens of the present invention showed a better anti-deposition. In addition, the contact angles of the ophthalmic lenses obtained in Example 1 to Example 8 were less than 40°, especially the contact angles of the ophthalmic lenses obtained in Example 1 and Example 4 were less than 20° showing excellent hydrophilicity of the lenses.

While the invention has been described by way of example(s) and in terms of the embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An ophthalmic lens comprising:
   a lens body; and
   an antimicrobial hydrophilic layer formed on the surface of the lens body, comprising tannic acid and a zwitterionic polymer, wherein the zwitterionic polymer is selected from the group consisting of a phosphorylcholine polymer, a sulfobetaine polymer, a carboxybetaine polymer and a mixed-charge polymer, or combinations thereof.

2. The ophthalmic lens as claimed in claim 1, wherein the zwitterionic polymer is selected from the group consisting of poly(2-methacryloyloxyethyl phosphorylcholine) (PMPC), poly(sulfobetaine methacrylate) (PSBMA) and poly(carboxybetaine methacrylate) (PCBMA), or combinations thereof.

3. The ophthalmic lens as claimed in claim 1, wherein the weight average molecular weight of the zwitterionic polymer is in the range of 10,000 to 300,000.

4. The ophthalmic lens as claimed in claim 1, wherein the lens body is made of a hydrogel or a silicon hydrogel.

5. A method for manufacturing an ophthalmic lens comprising:
   (a) providing a lens body;
   (b) immersing the lens body in a tannic acid solution, wherein the tannic acid solution comprises polydopamine; and
   (c) immersing the tannic acid treated lens body in a zwitterionic polymer solution, the zwitterionic polymer is selected from the group consisting of a phosphorylcholine polymer, a sulfobetaine polymer, a carboxybetaine polymer and a mixed-charge polymer, or combinations thereof.

6. The method for manufacturing an ophthalmic lens as claimed in claim 5, wherein the concentration of the tannic acid solution is between 250 ppm to 2500 ppm, and the concentration of the polydopamine in the tannic acid solution is between 1 ppm to 20 ppm.

7. The method for manufacturing an ophthalmic lens as claimed in claim 5, wherein in the step of (b), the tannic acid solution immersed with the lens body can be heated to a temperature of 30° C. to 80° C. for a time in the range of 5 minutes to 60 minutes.

8. The method for manufacturing an ophthalmic lens as claimed in claim 5, wherein in the step of (c), the concentration of the zwitterionic polymer solution is between 500 ppm to 3000 ppm.

9. The method for manufacturing an ophthalmic lens as claimed in claim 5, wherein the zwitterionic polymer solution can be heated to a temperature of 40° C. to 120° C. for a time in the range of 30 minutes to 120 minutes.

10. The method for manufacturing an ophthalmic lens as claimed in claim 5, wherein the zwitterionic polymer is selected from the group consisting of poly(2-methacryloyloxyethyl phosphorylcholine) (PMPC), poly(sulfobetaine methacrylate) (PCBMA) and poly(carboxybetaine methacrylate) (PCBMA), or combinations thereof.

11. A method for manufacturing an ophthalmic lens comprising:
   (a) providing a lens body; and (b) immersing the lens body in a solution comprising tannic acid, polydopamine and a zwitterionic polymer;

wherein the zwitterionic polymer is selected from the group consisting of a phosphorylcholine polymer, a sulfobetaine polymer, a carboxybetaine polymer and a mixed-charge polymer, or combinations thereof.

12. The method for manufacturing an ophthalmic lens as claimed in claim 11, wherein the concentrations of the tannic acid, the polydopamine, the zwitterionic polymer are respectively from 150 ppm to 1200 ppm, from 0.5 ppm to 20 ppm and from 150 ppm to 1200 ppm in the solution comprising tannic acid, polydopamine and zwitterionic polymer.

13. The method for manufacturing an ophthalmic lens as claimed in claim 11, wherein in step of (b), the solution comprising tannic acid, polydopamine and a zwitterionic polymer is heated to a temperature of 30° C. to 80° C. for a time in the range of 5 minutes to 60 minutes.

14. The method for manufacturing an ophthalmic lens as claimed in claim 11, wherein the weight average molecular weight of the zwitterionic polymer is in the range of 10,000 to 300,000.

* * * * *